(12) United States Patent  
Song et al.

(10) Patent No.: US 8,398,747 B2
(45) Date of Patent: Mar. 19, 2013

(54) PROCESSES FOR PURIFICATION OF ACETYLENE

(75) Inventors: Xuemei Song, Grand Island, NY (US); Lloyd Anthony Brown, East Amherst, NY (US); Thomas Thompson, Grand Island, NY (US)

(73) Assignee: Praxair Technology, Inc., Danbury, CT (US)

( * ) Notice: Subject to any disclaimer, the term of this patent is extended or adjusted under 35 U.S.C. 154(b) by 669 days.

(21) Appl. No.: 12/489,759

(22) Filed: Jun. 23, 2009

(65) Prior Publication Data

US 2010/0319536 A1 Dec. 23, 2010

(51) Int. Cl.
*B01D 53/02* (2006.01)

(52) U.S. Cl. .................. 95/96; 95/117; 95/139; 95/141; 95/145; 96/121; 96/131

(58) Field of Classification Search .............. 95/96, 118, 95/139, 140, 117, 130, 143, 145, 14, 141, 95/92; 96/130, 132, 144, 154, 121, 153, 96/136, 243, 131, 133; 422/190; 423/247
See application file for complete search history.

(56) References Cited

U.S. PATENT DOCUMENTS

| | | | | |
|---|---|---|---|---|
| 4,863,493 A * | 9/1989 | Kotani et al. | ...................... | 95/14 |
| 5,769,928 A * | 6/1998 | Leavitt | ............................... | 95/95 |
| 6,006,797 A * | 12/1999 | Bulow et al. | ....................... | 141/3 |
| 6,027,548 A * | 2/2000 | Ackley et al. | ....................... | 95/96 |
| 6,365,792 B1 * | 4/2002 | Stapf et al. | .................... | 585/539 |
| 7,011,695 B2 * | 3/2006 | Moreau et al. | ..................... | 95/96 |
| 7,264,651 B2 * | 9/2007 | Henzler et al. | ..................... | 95/96 |
| 7,524,358 B2 * | 4/2009 | Saxena et al. | .................... | 95/118 |
| 7,713,333 B2 * | 5/2010 | Rege et al. | ......................... | 95/96 |
| 7,820,556 B2 * | 10/2010 | Hsu et al. | ....................... | 438/758 |
| 8,182,589 B2 * | 5/2012 | Jha et al. | .......................... | 95/288 |
| 2008/0242912 A1 * | 10/2008 | Letessier et al. | .............. | 585/821 |
| 2009/0305516 A1 * | 12/2009 | Hsu et al. | ....................... | 438/780 |
| 2010/0069689 A1 * | 3/2010 | Maykut et al. | .................. | 585/16 |
| 2010/0154630 A1 * | 6/2010 | Jha et al. | .......................... | 95/15 |
| 2010/0297853 A1 * | 11/2010 | Hsu et al. | ....................... | 438/758 |

FOREIGN PATENT DOCUMENTS

| | | |
|---|---|---|
| FR | 285 3313 | 10/2008 |
| JP | 62285988 | 12/1987 |
| JP | 01-132535 | 5/1989 |
| JP | 2004 148257 A | 5/2004 |
| WO | WO 2004/089859 A2 | 10/2004 |

(Continued)

OTHER PUBLICATIONS

Miller, "Acetylene, Its Properties, Manufacture and Uses" published by Academic Press, New York and London, 1965, pp. 344, vol. 1.

(Continued)

*Primary Examiner* — Duane Smith
*Assistant Examiner* — Minh-Chau Pham
(74) *Attorney, Agent, or Firm* — Nilay S. Dalal (57) ABSTRACT

This invention relates in part to a process for producing high purity acetylene by withdrawing a crude acetylene stream from a storage source, and passing said stream through an adsorbent bed that contains layered adsorption media to selectively remove moisture, solvent and carbon dioxide from the stream, thereby producing the high purity acetylene. The adsorption media is regenerated in-situ. The high purity acetylene product is useful as a source material for depositing carbon and carbon-containing films in semiconductor applications.

20 Claims, 8 Drawing Sheets

FOREIGN PATENT DOCUMENTS

| | | |
|---|---|---|
| WO | WO 2008/120160 A1 | 10/2008 |
| WO | WO 2008/120160 A1 | 10/2008 |

OTHER PUBLICATIONS

IPR of WO 2004/089859-A2.

Saito Genji, Nakamura, T., "Purification of Acetylene by Two-Step Adsorption of Impurities on Zeolites and Activated Carbon", *Chemical Abstracts, Chemical Abstracts Service* (C A S), US, vol. 111, No. 19, Nov. 6, 1989, p. 675.

Siriwardane, R. et al, "Adsorption and Desorption of $CO_2$ on Solid Sorbents", *U.S. Department of Energy, National Energy Technology Laboratory*, URL:http://www.net1.doe.gov/publications/proceedings/01/carbon_seq/3b3.pdf, (retrieved Sep. 27, 2010), US, Mar. 9, 2008, pp. 1-14.

Unknown Author, XP002602241, "Molecular Sieve", *Wikipedia*, URL:http://en.wikipedia.org/wiki/Molecular_sieve (retrieved Sep. 27, 2010) US, Dec. 8, 2007, p. 1.

* cited by examiner

PROCESSES FOR PURIFICATION OF ACETYLENE

FIELD OF THE INVENTION

This invention relates to a process for removing carryover solvent, moisture and carbon dioxide from acetylene using adsorption media to produce high purity acetylene, and then regenerating in-situ the adsorption media for reuse. The high purity acetylene may be useful as a source material for depositing carbon and carbon-containing films in semiconductor applications.

BACKGROUND OF THE INVENTION

Acetylene is being used more and more as a source material for depositing carbon and carbon-containing films in semiconductor industry. Due to its instability, acetylene is conventionally dissolved in a solvent such as acetone, dimethylformamide (DMF) or N-methylpyrrolidone (NMP) and stored in cylinders containing porous material. When acetylene is withdrawn from the cylinder, an amount of solvent is carried over with the acetylene. The amount of solvent can range, depending on the cylinder temperature and pressure as well as the acetylene flow rate, from about 0.1 percent or less to about 10 percent or greater. The presence of solvent in acetylene is not desirable in applications such as semiconductor applications, especially for the emerging application of acetylene as a source gas for carbon film deposition in the electronic industry. The carryover solvent in acetylene reduces film deposition rate, which affects process uniformity and consistency.

Carbon-based adsorption is widely used in many industries as an effective means to remove volatile organic compounds from gas streams, such as air, nitrogen, etc. Activated carbon is a predominantly amorphous material having an extraordinarily large internal surface area that has been recognized as an effective means for solvent removal and recovery. Solvent removal from acetylene using activated carbon is disclosed, for example, in "Acetylene, Its Properties, Manufacture and Uses" published by Academic Press, New York and London, Vol. 1, page 344, 1965. After adsorption, the spent carbon may be then either disposed of in an approved manner or, more economically, the carbon bed is regenerated for reuse. The carbon bed should be regenerable in a manner so that the purification process can be cost effective.

Due to the catalyst effect of activated carbon, an oxidation reaction of solvent on activated carbon may happen, especially at elevated temperatures, during both adsorption and regeneration processes. Acetylene from an acetylene cylinder contains not only large amount of solvent but also moisture ranging from about 20 parts per million or less to about 100 parts per million or greater due to the presence of water in the solvent added to the acetylene cylinders, residual moisture in the cylinders prior to solvent addition and/or moisture in the acetylene charged to the cylinder. The presence of moisture in acetylene has a markable promoting effect on the oxidation reaction of the solvent on activated carbon. The oxidation reaction can foul the activated carbon so as to reduce its lifetime and also create new impurities in acetylene. For example, the oxidation of acetone may form acetic acid, carbon dioxide, carbon monoxide, and other impurities. Moisture is also an undesirable impurity in acetylene and reduces the efficiency of solvent adsorption on carbon.

The activated carbon not only has the possibility of holding carbon monoxide and carbon dioxide but also contains surface oxides that may produce carbon monoxide and carbon dioxide upon adsorption of a solvent. The carbon monoxide and carbon dioxide will contaminate acetylene when acetylene is passed through the activated carbon bed. Therefore, a need exists for minimizing the oxidation reaction of solvent on carbon and reducing byproduct impurities, for example, carbon dioxide, in acetylene, in order to produce high purity acetylene suitable for use in semiconductor applications. A need also exists for cost effectively regenerating activated carbon for reuse in the purification of acetylene.

SUMMARY OF THE INVENTION

This invention relates in part to a process for producing high purity acetylene comprising:

withdrawing a stream comprising acetylene and impurities from a storage source, said impurities comprising moisture and solvent;

providing an adsorbent bed containing adsorption media, said adsorption media comprising at least a first adsorption medium, a second adsorption medium and a third adsorption medium;

passing said stream through said first adsorption medium to selectively remove moisture from said stream, thereby producing a first partially purified stream;

passing said first partially purified stream through said second adsorption medium to selectively remove solvent from said first partially purified stream, thereby producing a second partially purified stream, said second partially purified stream containing other impurities, said other impurities comprising carbon dioxide; and passing said second partially purified stream through said third adsorption medium to selectively remove carbon dioxide from said second partially purified stream, thereby producing said high purity acetylene.

This invention also relates in part to a method for providing high purity acetylene to a work device, said method comprising:

withdrawing a stream comprising acetylene and impurities from a storage source, said impurities comprising moisture and solvent;

providing an adsorbent bed containing adsorption media, said adsorption media comprising at least a first adsorption medium, a second adsorption medium and a third adsorption medium;

passing said stream through said first adsorption medium to selectively remove moisture from said stream, thereby producing a first partially purified stream;

passing said first partially purified stream through said second adsorption medium to selectively remove solvent from said first partially purified stream, thereby producing a second partially purified stream, said second partially purified stream containing other impurities, said other impurities comprising carbon dioxide;

passing said second partially purified stream through said third adsorption medium to selectively remove carbon dioxide from said second partially purified stream, thereby producing said high purity acetylene; and providing the high purity acetylene to said work device.

This invention further relates in part to a high purity acetylene delivery system comprising:

a storage source containing acetylene and impurities, said impurities comprising moisture and solvent;

a distribution line disposed between said storage source and an adsorbent bed for distributing a stream of acetylene and impurities from said storage source to said adsorbent bed;

said adsorbent bed containing adsorption media capable of removing impurities from said stream;

said adsorption media comprising at least a first adsorption medium for selectively removing moisture from said stream, a second adsorption medium for selectively removing solvent from said stream, and a third adsorption medium for selectively removing other impurities from said stream; and a second distribution line disposed between said adsorbent bed and a work device for delivering high purity acetylene to said work device.

The invention provides a number of advantages. By using an activated carbon medium in an adsorbent bed and regenerating in-situ the carbon medium, the utilization of solvent-based acetylene in electronics applications can be increased significantly. The capital cost of the adsorbent bed and carbon medium is much less than for some other techniques such as cold traps. The operation of the adsorbent bed is simple especially if it is integrated with the acetylene gas delivery system so that there is minimal additional labor required to operate the bed. The use of a first adsorption medium, e.g., a molecular sieve, to selectively remove moisture prior to solvent removal using a second adsorption medium, e.g., activated carbon, and the use of a third adsorption medium, e.g., a molecular sieve, to remove carbon dioxide after solvent removal, provides higher purity acetylene compared to the use of activated carbon only. The removal of moisture from acetylene prior to passing the acetylene stream through activated carbon can reduce the reaction of solvent on carbon. The process can also improve the lifetime of activated carbon. The higher purity acetylene improves carbon film deposition rate/quality and thereby reduces cost. The high purity acetylene can be used for semiconductor applications such as amorphous carbon hardmask film deposition.

DETAILED DESCRIPTION OF THE INVENTION

As indicated above, this invention relates in part to a process for producing high purity acetylene comprising:

withdrawing a stream comprising acetylene and impurities from a storage source, said impurities comprising moisture and solvent;

providing an adsorbent bed containing adsorption media, said adsorption media comprising at least a first adsorption medium, a second adsorption medium and a third adsorption medium;

passing said stream through said first adsorption medium to selectively remove moisture from said stream, thereby producing a first partially purified stream;

passing said first partially purified stream through said second adsorption medium to selectively remove solvent from said first partially purified stream, thereby producing a second partially purified stream, said second partially purified stream containing other impurities, said other impurities comprising carbon dioxide; and passing said second partially purified stream through said third adsorption medium to selectively remove carbon dioxide from said second partially purified stream, thereby producing said high purity acetylene.

The above process can further comprise:
stopping the passing of said stream through said adsorbent bed;
regenerating in-situ said adsorption media, and
removing desorbed impurities from said adsorbent bed.

This invention may be applied to any solvents used to store acetylene in an acetylene cylinder such as DMF, acetone, NMP, and the like. This invention provides an improved process for selectively removing impurities from acetylene using adsorption media, and in-situ regeneration of the adsorption media for reuse. The process of this invention reduces the amount of impurities in acetylene such as, but not limited to, solvents (e.g., DMF, acetone and NMP), moisture, carbon dioxide, and other impurities, to provide high purity acetylene. The high purity acetylene has less than about 1000 parts per million (ppm) volume, preferably less than about 100 ppm volume, more preferably less than about 10 ppm volume, and most preferably less than about 1 ppm volume of solvent. The high purity acetylene has less than about 100 ppm volume, preferably less than about 10 ppm volume, and more preferably less than about 1 ppm volume of moisture. The high purity acetylene has less than about 100 ppm volume, preferably less than about 10 ppm volume, and more preferably less than about 1 ppm volume of carbon dioxide. The high purity acetylene has less than about 100 ppm volume, preferably less than about 10 ppm volume, and more preferably less than about 1 ppm volume of other impurities.

Figure 1:
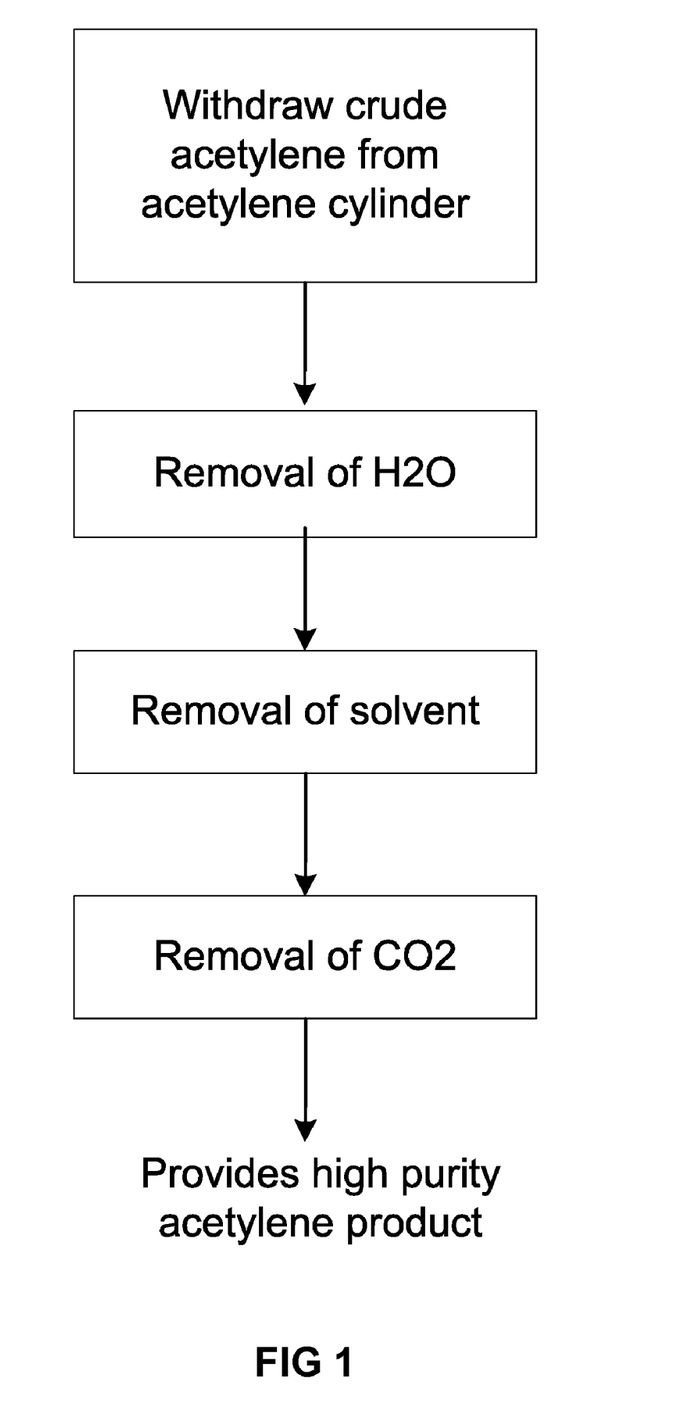
FIG. 1 depicts a flow diagram for producing high purity acetylene in accordance with a process of this invention.

FIG. 1 is a flow diagram of a purification process of this invention wherein a crude acetylene stream is drawn from acetylene sources, typically an acetylene cylinder. The crude acetylene stream may contain, for example, 100 ppm or greater of solvent (e.g., acetone, DMF and NMP), 10 ppm or greater of moisture, and less than 1 ppm or greater of carbon dioxide. The crude acetylene stream is passed through a first portion of adsorbent material to selectively remove moisture contained therein and provides a partially purified acetylene stream. The first portion of adsorbent material may be any material that can selectively remove moisture from a crude acetylene stream. Suitable materials include commercially available materials such as molecular sieves. Illustrative materials may include, but are not limited to, molecular sieves 4A(NaA), 5A(CaA), 13X (NaX), NaY, NaF, activated alumina, silicon gel and mixtures thereof. The most preferred adsorbent material as first portion for moisture removal is molecular sieve 13X. The crude acetylene is passed through the first portion of adsorbent at temperatures ranging from about −70° C. to about 100° C. and pressures at about 15 psig or less. The most preferred temperature is at room temperature.

The partially purified acetylene is then passed through a second portion of adsorbent material to selectively remove solvent contained therein and to provide a purified solvent-free acetylene stream. The second portion of adsorbent material may be any material that can selectively remove solvent from a crude acetylene stream. Suitable materials include conventional materials that are available commercially such as activated carbon. Preferred adsorption materials include, but are not limited to, activated carbon. The activated carbon can be any commercial available types, such as water or acid washed, extruded or granular activated carbon produced from nutshells, coal, wood and the like. The crude acetylene is passed through the second portion of adsorbent at temperatures ranging from about −70° C. to about 100° C. and pressures of about 15 psig or less. The most preferred temperature is at room temperature.

The solvent-free acetylene is then passed through a third portion of adsorbent material to selectively remove carbon dioxide contained therein and provide a high purity acetylene stream. The third portion of adsorbent may be any material that can selectively remove carbon dioxide from a crude acetylene stream. Suitable materials include commercially available materials such as molecular sieves. Illustrative materials may include, but are not limited to, molecular sieves 4A(NaA), 5A(CaA), 13X (NaX), NaY, NaF, activated alumina, silicon gel and mixtures thereof. The most preferred adsorbent material as third portion for carbon dioxide removal from acetylene is molecular sieve 13X. The crude acetylene is passed through the third portion of adsorbent at temperatures ranging from about −70° C. to about 100° C. and pressures at about 15 psig or less. The most preferred temperature is at room temperature.

In an embodiment, the first adsorption medium comprises a molecular sieve, the second adsorption medium comprises activated carbon, and the third adsorption medium comprises a molecular sieve. In particular, the first adsorption medium comprises a molecular sieve 4A(NaA), 5A(CaA), 13X(NaX), NaY, NaF, activated alumina, silicon gel or mixtures thereof, the second adsorption medium comprises activated carbon, and the third adsorption medium comprises a molecular sieve 4A(NaA), 5A(CaA), 13X(NaX), NaY, NaF, activated alumina, silicon gel or mixtures thereof.

Figure 2:
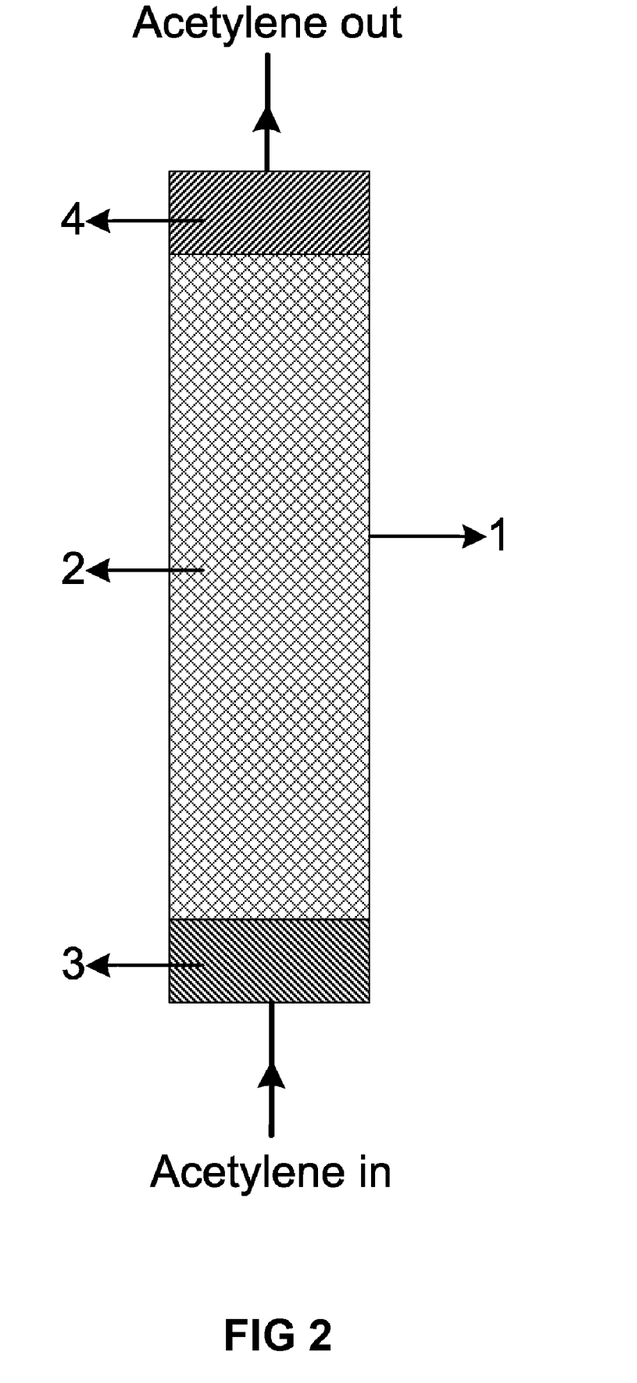
FIG. 2 depicts an adsorption bed column containing adsorption media used in producing high purity acetylene.

FIG. 2 depicts an adsorption vessel 1 with layered adsorbent materials used to selectively adsorb contaminants from feed acetylene. A portion of the adsorbent material is used to selectively adsorb moisture present in the feed acetylene in the moisture adsorption zone 3 at the bottom of adsorption vessel 1. Solvent adsorption zone 2, above moisture adsorption zone 3, is filled with adsorbent material used to selectively adsorb solvent in acetylene. Carbon dioxide adsorption zone 4 at the top of adsorption vessel 1 is filled with adsorbent material used to selectively remove carbon dioxide from acetylene. A conduit is connected to the bottom of said adsorption vessel 1 for the introduction of crude acetylene stream during adsorption step and for the discharge of purge gas and contaminants selectively removed from the acetylene during the desorption-regeneration step. A conduit is connected to the top of said adsorption vessel 1 for the removal of purified acetylene from adsorption vessel 1 during the adsorption step and for the introduction of purge gas to the adsorption vessel during the desorption-regeneration step.

The adsorbent column can be configured, for example, by sizing the adsorbent column based on the use of the number of acetylene cylinders, and by automatically or manually switching the adsorbent column for regeneration when the cylinder switches. The amount of each adsorbent medium in each adsorption zone may vary depending upon a variety of factors such as, the flow rate of the acetylene stream, the amount of impurities contained within the acetylene, and the like.

In an embodiment of this invention, the purification may be conducted in discrete steps using separated adsorbent vessels. For example, a first adsorption vessel may contain a first adsorbent medium selective for moisture removal; a second adsorption vessel may contain a second adsorbent medium selective for solvent removal; and a third adsorption vessel may contain a third adsorbent medium selective for carbon dioxide removal. One or more other adsorbents or filtration media can be used in conjunction with the adsorption media above to remove various impurities from the acetylene stream, such as particle removal. The adsorbents can be mixed or layered one after another. Other impurities, such as phosphine, arsine, sulfur compounds, and the like may also be removed by the adsorbent media. The adsorbents can be conventional materials known in the art and can be used in amounts that may vary depending upon a variety of factors such as the flow rate of the acetylene stream, the amount of impurities contained within the acetylene, and the like.

The use of adsorption media, e.g., activated carbon and molecular sieves, provides a higher purity acetylene than conventional techniques such as cold traps. The removal of moisture prior to solvent, e.g., acetone, removal not only improves acetylene purity but also prevents moisture from enhancing the oxidation reaction of solvent on activated carbon which reduces carbon's lifetime and produces contaminants. The removal of carbon dioxide after solvent adsorption further improves acetylene impurities by removing any reaction byproducts if any.

Adsorption conditions, such as temperature, pressure and flow rate, may also vary greatly and any suitable combination of such conditions may be employed herein. The adsorption conditions should be sufficient to remove moisture, solvent and carbon dioxide from the crude acetylene stream. The adsorption temperature may range from about −70° C. to about 100° C., preferably at room temperature or below. The adsorption pressure may range from about atmospheric pressure to about 250 psig, preferably from about atmospheric pressure to about 15 psig. The crude acetylene stream can be withdrawn from the storage source, e.g., cylinder, at a rate of from about 0.1 liters per minute (lpm) to about 80 lpm. More cylinders may be bundled for higher flow rates.

In an embodiment, the process of this invention involves passing a crude acetylene stream through an adsorption bed containing adsorption media at a temperature and pressure sufficient to adsorb at least moisture, solvent and carbon dioxide impurities onto the adsorption media, shutting off the flow of the crude acetylene stream to the adsorption bed, and in situ regenerating the adsorption bed at a temperature, pressure and time sufficient to desorb the impurities from the adsorption media.

The adsorbent regeneration is typically carried out at either high temperature and/or low pressure. Activated carbon is generally regenerated by passing hot steam and/or inert gas through the carbon medium. The adsorbent bed containing layers of activated carbon and molecular sieves may be regenerated by purging using a purge gas, e.g. nitrogen or acetylene, or evacuating the adsorption bed at elevated temperatures. Generally, regeneration by using purge gas provides higher regeneration efficiency than that when evacuation is used. However, when inert gas, e.g. nitrogen, is used as purge gas, nitrogen will be introduced into the system as an impurity that is difficult to be removed down to ppm levels. It is preferred that acetylene be used as a purge gas for the regeneration or a combination of inert gas and acetylene, e.g. nitrogen first and acetylene last.

Alternatively, regeneration by evacuation may be used. Since the forces bonding the solvent to the surface of the adsorption medium are intermolecular bonds that are very weak, solvent may vaporize at high temperature and can be evacuated by drawing a vacuum on the adsorbent bed. The process of this invention avoids contamination that results from hot steam or inert purge gases. The adsorbent bed may be evacuated using any vacuum generating means, such as vacuum pump, Venturi pump, and the like. Due to the instability of acetylene, a Venturi pump rather than a vacuum pump is preferred to evacuate the adsorbent bed. In a particular embodiment, the regeneration steps involve switching the adsorbent vessel to be regenerated to the exhaust or scrubber system, turning on the Venturi pump, and applying a heating means for maintaining the adsorbent bed at a temperature above the boiling point of the solvent. At reduced pressures, the boiling temperature of the solvent can be lower than that at atmospheric pressure. Nitrogen rather than air is preferred to run the Venturi pump due to the safety concern of acetylene. The evacuation can involve pulling a vacuum on the adsorbent bed in a direction opposite to the direction that the stream passed through the adsorbent bed, and removing desorbed impurities from the adsorbent bed.

Regeneration conditions, such as temperature, pressure and evacuation time, may also vary greatly and any suitable combination of such conditions may be employed herein. The regeneration conditions should be sufficient to remove desorbed solvent from the adsorbent bed. The regeneration may be accomplished by evacuating the adsorbent bed by suitable vacuum-producing means at a temperature above the boiling temperature of the solvent. The regeneration temperature may range from about room temperature to about 350° C., preferably from about 50° C. to about 250° C., and most preferably from about 100° C. to about 200° C. The regeneration vacuum may be less than atmospheric pressure, preferably less than 200 torr, and most preferably less than 50 torr. The evacuating time of the adsorption bed depends on the bed size and can range from about 30 to about 720 minutes, preferably from about 60 to 360 minutes.

In accordance with the process of this invention, high purity acetylene is produced that contains less than about 1000 parts per million (ppm) of solvent, preferably less than about 100 ppm of solvent, and more preferably less than about 10 ppm of solvent. Crude acetylene is passed through adsorption media and the adsorption media undergoes in-situ regeneration after adsorption to improve on-line time and reduce operating cost. The high purity acetylene further contains less than about 100 ppm of moisture, preferably less than 10 ppm of moisture, and more preferably less than 1 ppm of moisture. The high purity acetylene also contains less than about 100 ppm of carbon dioxide, preferably less than about 10 ppm of carbon dioxide, and more preferably less than about 1 ppm of carbon dioxide. The regeneration may be accomplished by evacuating the adsorbent bed at a temperature above the boiling temperature of the solvent.

As indicated above, this invention relates in part to a method for providing high purity acetylene to a work device, said method comprising:

withdrawing a stream comprising acetylene and impurities from a storage source, said impurities comprising moisture and solvent;

providing an adsorbent bed containing adsorption media, said adsorption media comprising at least a first adsorption medium, a second adsorption medium and a third adsorption medium;

passing said stream through said first adsorption medium to selectively remove moisture from said stream, thereby producing a first partially purified stream;

passing said first partially purified stream through said second adsorption medium to selectively remove solvent from said first partially purified stream, thereby producing a second partially purified stream, said second partially purified stream containing other impurities, said other impurities comprising carbon dioxide;

passing said second partially purified stream through said third adsorption medium to selectively remove carbon dioxide from said second partially purified stream, thereby producing said high purity acetylene; and providing the high purity acetylene to said work device.

The method further comprises:

stopping the passing of said stream through said adsorbent bed;

regenerating in-situ said adsorption media, and removing desorbed impurities from said adsorbent bed.

The process of this invention reduces moisture, solvent and carbon dioxide in acetylene discharged from storage vessels, e.g., one or more cylinders, in order to provide high purity acetylene in a cost effective way.

The process of this invention can further comprise:

providing a second adsorbent bed in parallel to said adsorbent bed, said second adsorbent bed containing adsorption media, said adsorption media comprising at least a first adsorption medium, a second adsorption medium and a third adsorption medium;

stopping the passing of said stream through said adsorbent bed;

passing said stream through said first adsorption medium of said second adsorbent bed to selectively remove moisture from said stream, thereby producing a first partially purified stream of said second adsorbent bed;

passing said first partially purified stream of said second adsorbent bed through said second adsorption medium of said second adsorbent bed to selectively remove solvent from said first partially purified stream, thereby producing a second partially purified stream of said second adsorbent bed, said second partially purified stream of said second adsorbent bed containing other impurities, said other impurities comprising carbon dioxide; and passing said second partially purified stream of said second adsorbent bed through said third adsorption medium of said second adsorbent bed to selectively remove carbon dioxide from said second partially purified stream of said second adsorbent bed, thereby producing said high purity acetylene;

regenerating in-situ said adsorption media of said adsorbent bed; and removing desorbed impurities from said adsorbent bed.

In particular, a second adsorbent bed can be provided in parallel with the first adsorbent bed. The passing of the stream comprising acetylene and solvent can be switched from the first adsorbent bed to the second adsorbent bed while the first adsorbent bed is being regenerated. The flow of the stream can be switched selectively between the first and second adsorbent beds based upon the amount of high purity acetylene provided to the work device, e.g., semiconductor processing tool. High purity acetylene can be supplied to a work device from the second adsorbent bed while the first adsorbent bed is regenerating. Likewise, a high purity acetylene product can be supplied to a work device from the first adsorbent bed while the second adsorbent bed is regenerating. More adsorbent beds may be installed in parallel for high flow rates and less regeneration time.

Figure 3:
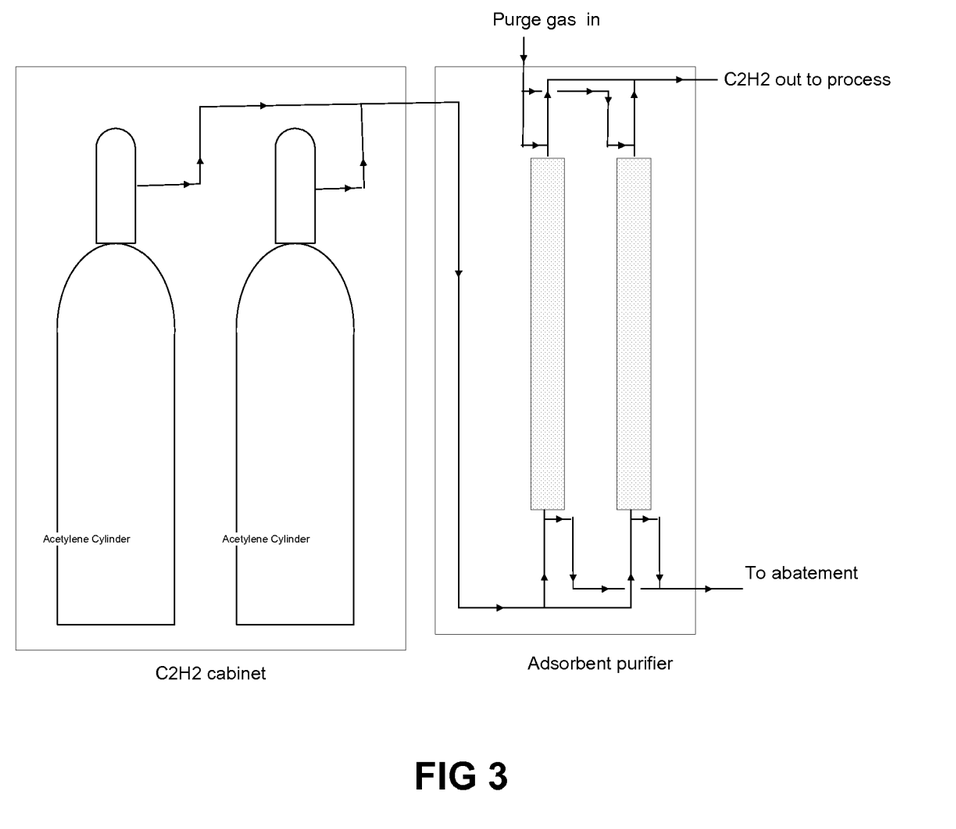
FIG. 3 is a schematic representation of an adsorbent bed or purifier setup with acetylene-containing cylinders.

Providing solvent-free acetylene using a point-of-use adsorbent bed with an acetylene gas cabinet is unique. The adsorbent bed may be positioned inside the acetylene gas cabinet or in a separate cabinet proximate to the acetylene cabinet. FIG. 3 shows an adsorbent bed or purifier setup in one cabinet with acetylene-containing cylinders in a separate cabinet. The adsorbent bed may be controlled independently or integrated with the acetylene gas delivery system. For certain applications such as carbon hardmask deposition, it may be desirable to integrate the adsorbent bed with the acetylene gas delivery system. Usually the adsorbent column is switched automatically by setting up a switching time or by monitoring the breakthrough. Since the content of solvent and moisture in acetylene changes as the acetylene cylinder pressure changes, it is difficult to determine the column switch by time. Additionally, it is costly to monitor the breakthrough. The simplest method is to size the adsorbent column so that it can be automatically or manually switched for regeneration when the acetylene cylinder or number of acetylene cylinders is switched.

For example, a 4 inch×4 foot adsorption column containing layered adsorbent materials in accordance with this invention, e.g., a first layer of about 0.6 kilograms (kg) of molecular sieve 13X, a second layer of about 4.8 kilograms of activated carbon, and a third layer of about 0.6 kilograms (kg) of molecular sieve 13X, should be sufficient to purify the contents of an acetone-based A420 acetylene cylinder (Praxair AHM grade). The column may be sized as needed if more cylinders are connected. Because the column is sized properly, it may be switched automatically or manually when the cylinder switches. Additionally, the columns may be regenerated automatically after switching. The column may be equipped with high temperature and high pressure shutdown. The desorbed solvent from the adsorbent bed may be collected by using water trap, cold trap, or any suitable exhaust scrubber. More than one purification column may be used to allow one or more to be undergoing regeneration while one or more other columns are on-line.

The adsorbent column may be used alone or combined with other techniques, such as a cold trap. If a cold trap is used, it is preferred that acetylene with carryover acetone passes through the cold trap first so that the majority of acetone condenses inside the cold trap and then passes through an adsorbent bed containing layered adsorbent materials in accordance with this invention, so that impurities, such as moisture, solvent, carbon dioxide, and the like, are further reduced to a lower level.

As indicated above, this invention relates in part to a high purity acetylene delivery system comprising:

a storage source containing acetylene and impurities, said impurities comprising moisture and solvent;

a distribution line disposed between said storage source and an adsorbent bed for distributing a stream of acetylene and impurities from said storage source to said adsorbent bed;

said adsorbent bed containing adsorption media capable of removing impurities from said stream;

said adsorption media comprising at least a first adsorption medium for selectively removing moisture from said stream, a second adsorption medium for selectively removing solvent from said stream, and a third adsorption medium for selectively removing other impurities from said stream; and a second distribution line disposed between said adsorbent bed and a work device for delivering high purity acetylene to said work device.

The high purity acetylene delivery system may further comprise:

a second adsorbent bed disposed on said distribution line in parallel with said adsorbent bed;

said second adsorbent bed containing adsorption media capable of removing impurities from said stream;

said adsorption media comprising at least a first adsorption medium for selectively removing moisture from said stream, a second adsorption medium for selectively removing solvent from said stream, and a third adsorption medium for selectively removing other impurities from said stream; and a third distribution line disposed between said second adsorbent bed and a work device for delivering the high purity acetylene to said work device.

The high purity acetylene may be useful as a source material for depositing carbon and carbon-containing films in semiconductor applications. In particular, the high purity acetylene can be used for semiconductor applications such as amorphous carbon hardmask film deposition.

Various modifications and variations of this invention will be obvious to a worker skilled in the art and it is to be understood that such modifications and variations are to be included within the purview of this application and the spirit and scope of the claims.

The invention will be illustrated in more detail by the following examples, but it is to be understood that the present invention is not limited to the examples. Granular activated carbon (4×8 mesh) produced from coconut shells manufactured by Norit was used for the test. The concentrations of acetone, moisture and carbon dioxide were monitored using an FT-IR equipped with an MCT detector (MAGNA-IR 760 from Nicolet).

Example 1

Acetone Carryover Removal from Nitrogen

Figure 4:
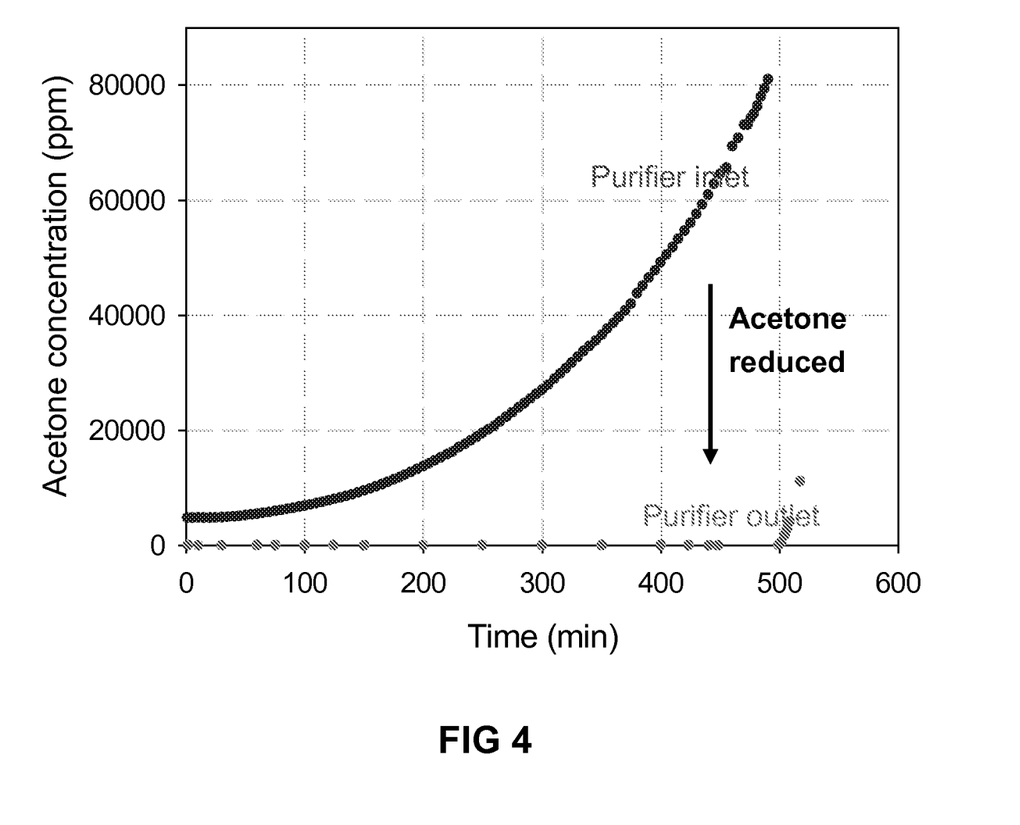
FIG. 4 graphically depicts acetone carryover removal from nitrogen using an activated carbon adsorbent bed or purifier from Example 1 below.

A preliminary test was done using nitrogen. Nitrogen containing acetone ranging from 5000 ppm to 8% was continuously passed through a stainless steel bed (2-inch inner diameter and 5-feet length) that contained 1.87 kilograms (kg) of activated carbon. The nitrogen pressure was controlled at 13 pounds per square inch gauge (psig) and flow rate was 12 standard liters per minute (slpm). Nitrogen feed to bed was stopped when acetone breakthrough was observed. A total of 0.466 kg of acetone was collected by the carbon column. The acetone concentration profile over time is shown in FIG. 4.

Example 2

Acetone Carryover Removal from Acetylene

Figure 5:
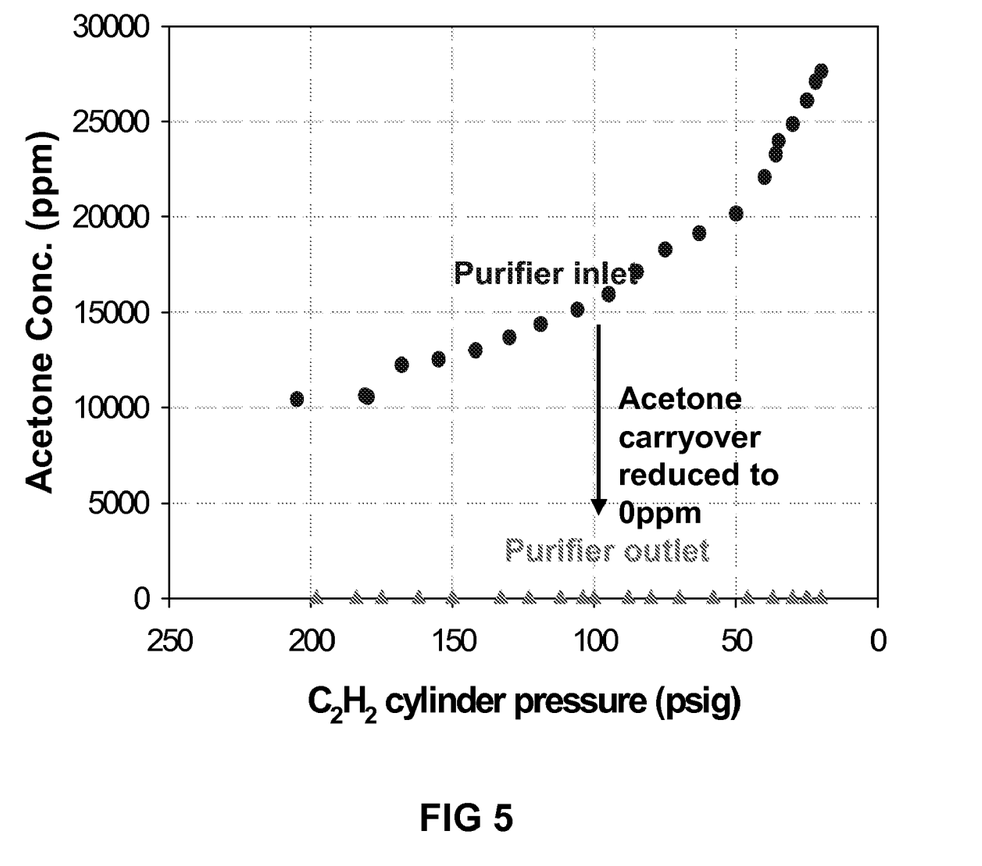
FIG. 5 graphically depicts acetone carryover removal from acetylene using activated carbon adsorbent bed or purifier from Example 2 below.

Crude acetylene from an acetone-based A390 AA grade acetylene cylinder was continuously passed through a stainless steel column (2 inch inner diameter and 3 feet length) that contained 1.12 kg of activated carbon. The pressure of acetylene was regulated at 13 psig and flow rate was 12 slpm. Acetylene cylinder temperature was not controlled and varied with ambient temperature. Ambient temperature was 20° C. initially and dropped to 15° C. at the end of the test. The maximum temperature difference between the acetylene cylinder and ambient was around 6° C. The acetylene flow to the carbon bed was stopped when the acetylene cylinder pressure dropped to 20 psig. Due to the low acetylene cylinder temperature caused by low ambient temperature as well as continuously high acetylene flow, acetone concentration in withdrawn acetylene was lower than predicted. A total of 0.26 kg of acetone was collected by activated carbon. The FTIR analysis on the acetylene at the purifier outlet showed that the acetone concentration had been lowered to less than 1 ppm and no breakthrough was observed as shown in FIG. 5.

Figure 6:
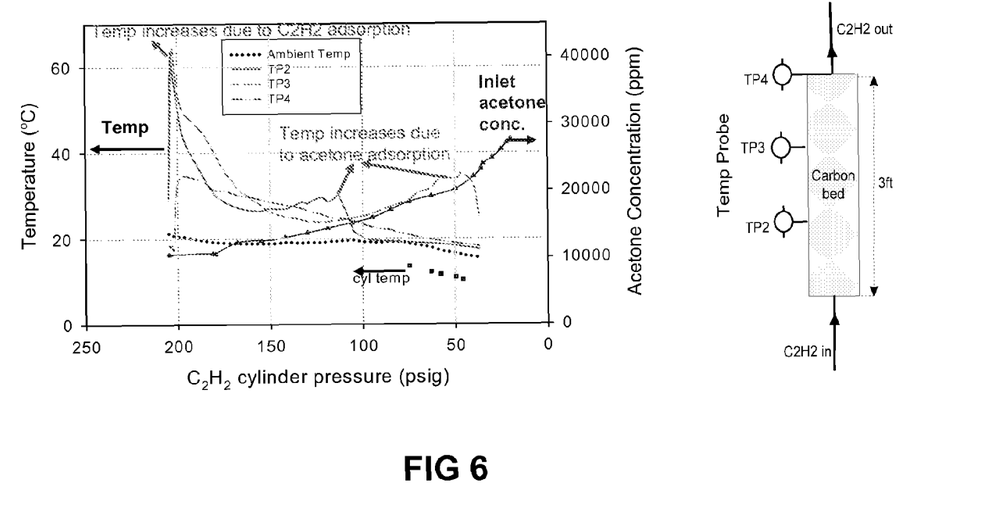
FIG. 6 graphically depicts a temperature profile of a carbon bed when acetylene was passed through from Example 2 below.

Once acetylene was fed to the carbon purifier, the purifier temperature increased sharply to about 63° C. due to initial acetylene adsorption and then was cooled down by the incoming acetylene flow. The bed temperature then increased slowly due to acetone adsorption that displaced the acetylene adsorbed. Overall, the temperature exotherm of the purifier was manageable. The temperature profile is shown in FIG. 6.

Based on data from the examples above, the amount of carbon needed for acetone removal from various types of acetylene cylinders may be calculated. For example, based on a simulated result, the maximum acetone released from an A420 cylinder is around 0.5-0.9 kg. The carbon needed to remove the released acetone from one A420 cylinder would be around 3.7 kg. Due to low packing density, a 4 inch by 4 foot column containing around 5.9 kg of carbon would be good for the application.

Example 3

A nitrogen stream containing 2% acetone and 260 ppm moisture was passed through two columns of 1.5 inch diameter and 8 inch length, respectively. One column was packed with activated carbon only and the other was packed with layered adsorbents containing activated carbon and molecular sieve 13X, respectively. The nitrogen inlet stream did not contain carbon dioxide or carbon monoxide. The nitrogen inlet flow rate was 12 slpm. The two columns were activated by maintaining at a temperature of 200° C. and purging with nitrogen for a period of 5 hours. The amount and types of adsorbents in the columns are shown in table below. 13X molecular sieve is APG3 (8×12 mesh sphere) manufactured by UOP. The activated carbon is 4×8 mesh coconut based granular carbon manufactured by Norit.

| Column No. | Adsorbents |
| --- | --- |
| #1 (Activated carbon) | Activated carbon (139 grams) |
| #2 (Layered adsorbents) | 1st portion: 13X molecular sieve (15 grams) |
| | 2nd portion: activated carbon (110 grams) |
| | 3rd portion: 13X molecular sieve (15 grams) |

Figure 7:
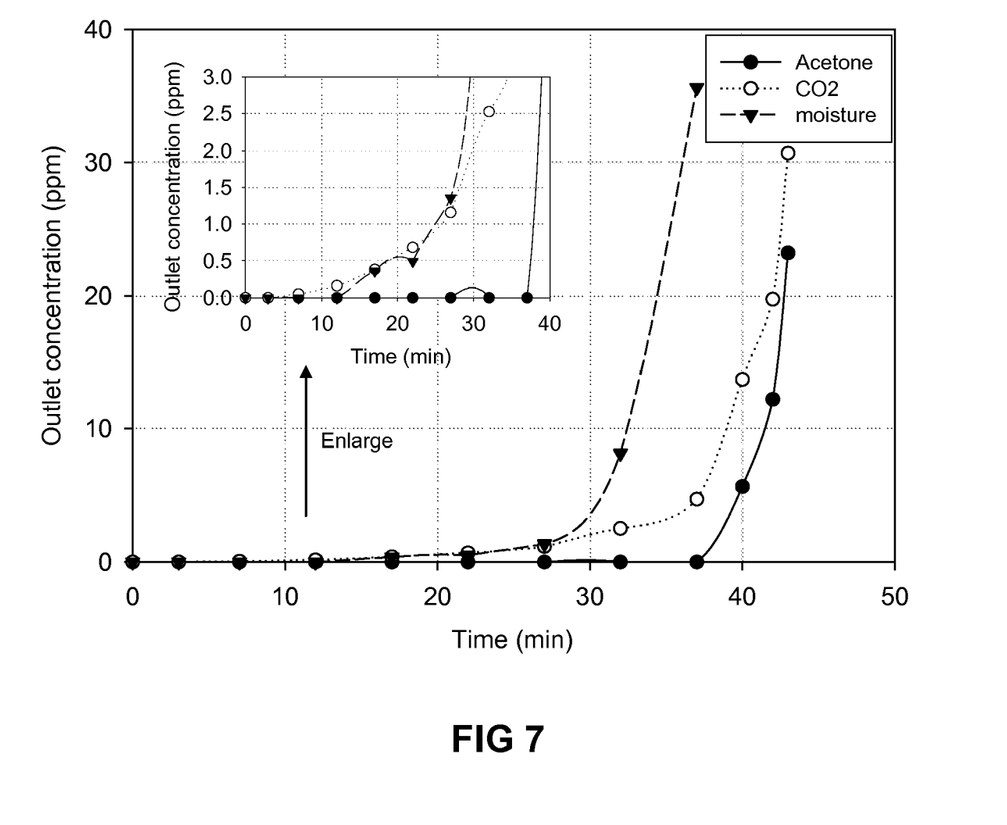
FIG. 7 graphically depicts outlet concentrations of acetone, moisture and carbon dioxide over time in nitrogen using an activated carbon adsorbent bed or purifier from Example 3 below.
Figure 8:
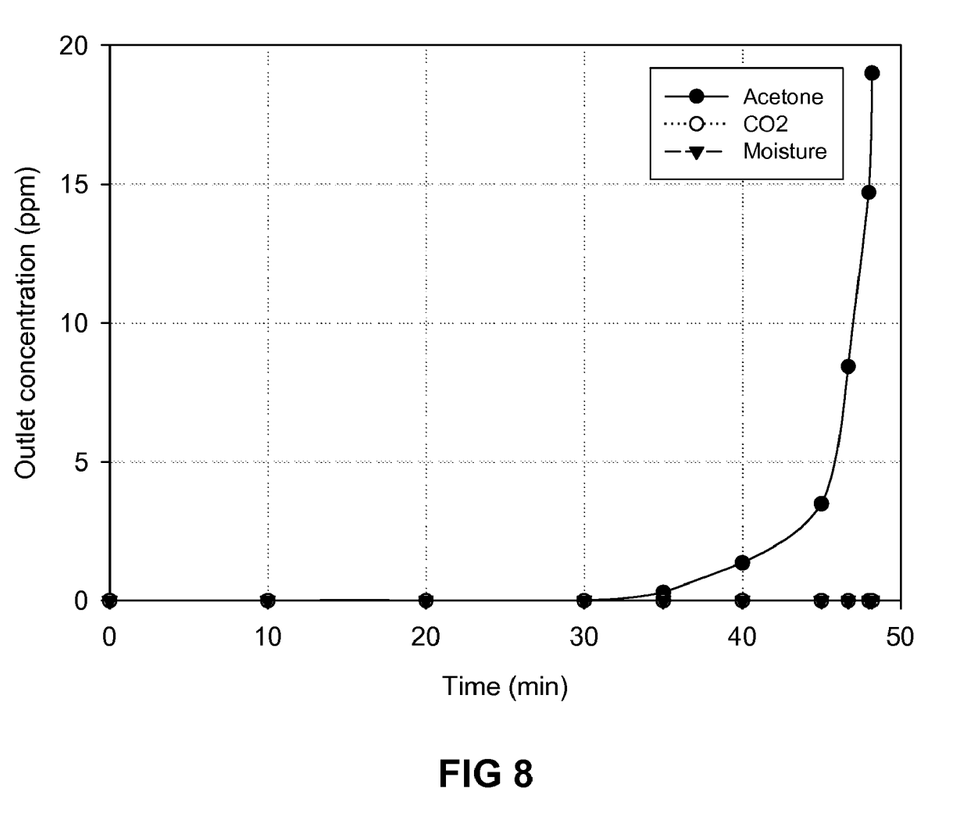
FIG. 8 graphically depicts outlet concentrations of acetone, moisture and carbon dioxide over time in nitrogen using a layered adsorbent bed or purifier of activated carbon and molecular sieve from Example 3 below.

The concentrations of acetone, moisture and carbon dioxide from the purifier outlet are shown in FIG. 7 (column #1) and FIG. 8 (column #2). By using molecular sieve 13X on the bottom and headspace of the purifier, moisture and carbon dioxide were removed completely. When acetone breakthrough was observed, the adsorption process was stopped.

Example 4

Regeneration of Activated Carbon-Vacuum vs. Nitrogen Purge

Two identical 2 inch by 5 foot carbon columns containing 1.87 kg of carbon from Example 1 was used for the regeneration tests. The regeneration tests were done by using both hot nitrogen purge and evacuating the column at 200° C., respectively. In both cases, the column temperature was ramped at 6° C./minute and then maintained at a temperature of 200° C. When purge nitrogen was used, the nitrogen flow rate was 12 liters per minute. The column pressure was 13 psig. When vacuum regeneration was used, the vacuum inside the column was maintained at 3.8 psia at 200° C. The regeneration process was allowed to last for a period of 2 hours. The evacuation was done by using a Venturi pump (model:VG-015-00-00 manufactured by GAST. Five cycles of regenerations were done in each case. When purge nitrogen was used, around 95%-98% of acetone adsorbed was removed. When evacuation method was used, around 60%-65% of acetone adsorbed was removed.

The invention claimed is:

1. A process for producing high purity acetylene comprising:
    withdrawing a stream comprising acetylene and impurities from a storage source, said impurities comprising moisture and solvent;
    providing an adsorbent bed containing adsorption media, said adsorption media comprising at least a first adsorption medium, a second adsorption medium and a third adsorption medium;
    passing said stream through said first adsorption medium to selectively remove moisture from said stream, thereby producing a first partially purified stream;
    passing said first partially purified stream through said second adsorption medium to selectively remove solvent from said first partially purified stream, thereby producing a second partially purified stream, said second partially purified stream containing other impurities, said other impurities comprising carbon dioxide; and
    passing said second partially purified stream through said third adsorption medium to selectively remove carbon dioxide from said second partially purified stream, thereby producing said high purity acetylene.

2. The process of claim 1 further comprising:
    stopping the passing of said stream through said adsorbent bed;
    regenerating in-situ said adsorption media, and
    removing desorbed impurities from said adsorbent bed.

3. The process of claim 1 wherein said first adsorption medium comprises a molecular sieve, said second adsorption medium comprises activated carbon, and said third adsorption medium comprises a molecular sieve.

4. The process of claim 1 wherein said first adsorption medium comprises a molecular sieve 4A(NaA), 5A(CaA), 13X(NaX), NaY, NaF, activated alumina, silicon gel or mixtures thereof, said second adsorption medium comprises activated carbon, and said third adsorption medium comprises a molecular sieve 4A(NaA), 5A(CaA), 13X(NaX), NaY, NaF, activated alumina, silicon gel or mixtures thereof.

5. The process of claim 1 wherein passing said stream through said adsorbent bed is carried out at a temperature, pressure and flow rate sufficient to remove solvent from said stream.

6. The process of claim 1 wherein passing said stream through said adsorbent bed is carried out at a temperature of from about −70° C. to about 100° C. and a pressure of from about atmospheric to about 250 psig.

7. The process of claim 1 wherein regenerating in-situ said adsorption media comprises evacuating said adsorbent bed, said evacuating comprising drawing a vacuum on said adsorbent bed in a direction opposite to the direction that said stream passed through said adsorbent bed.

8. The process of claim 1 wherein regenerating in-situ said adsorption medium is carried out at a temperature, pressure and evacuating time sufficient to remove desorbed impurities from said adsorbent bed.

9. The process of claim 1 wherein regenerating in-situ said adsorption medium is carried out at a temperature of from about ambient temperature to about 350° C. and a pressure less than about atmospheric pressure.

10. The process of claim 1 further comprising:
providing a second adsorbent bed in parallel to said adsorbent bed, said second adsorbent bed containing adsorption media, said adsorption media comprising at least a first adsorption medium, a second adsorption medium and a third adsorption medium;
stopping the passing of said stream through said adsorbent bed;
passing said stream through said first adsorption medium of said second adsorbent bed to selectively remove moisture from said stream, thereby producing a first partially purified stream of said second adsorbent bed;
passing said first partially purified stream of said second adsorbent bed through said second adsorption medium of said second adsorbent bed to selectively remove solvent from said first partially purified stream, thereby producing a second partially purified stream of said second adsorbent bed, said second partially purified stream of said second adsorbent bed containing other impurities, said other impurities comprising carbon dioxide; and
passing said second partially purified stream of said second adsorbent bed through said third adsorption medium of said second adsorbent bed to selectively remove carbon dioxide from said second partially purified stream of said second adsorbent bed, thereby producing said high purity acetylene;
regenerating in-situ said adsorption media of said adsorbent bed; and
removing desorbed impurities from said adsorbent bed.

11. The process of claim 10 further comprising switching the flow of said stream from said second adsorbent bed to said adsorbent bed.

12. The process of claim 10 wherein said storage source comprises one or more cylinders.

13. The process of claim 12 further comprising sizing said adsorbent bed per the size and number of cylinders and automatically or manually switching said adsorbent bed for regeneration when any of said number of cylinders is switched.

14. The process of claim 1 wherein said high purity acetylene has less than about 1000 parts per million volume of solvent, less than about 100 parts per million volume of moisture, and less than about 100 parts per million volume of carbon dioxide.

15. The process of claim 1 wherein the solvent comprises acetone, dimethylformamide (DMF) or N-methylpyrrolidone (NMP).

16. A method for providing high purity acetylene to a work device, said method comprising:
withdrawing a stream comprising acetylene and impurities from a storage source, said impurities comprising moisture and solvent;
providing an adsorbent bed containing adsorption media, said adsorption media comprising at least a first adsorption medium, a second adsorption medium and a third adsorption medium;
passing said stream through said first adsorption medium to selectively remove moisture from said stream, thereby producing a first partially purified stream;
passing said first partially purified stream through said second adsorption medium to selectively remove solvent from said first partially purified stream, thereby producing a second partially purified stream, said second partially purified stream containing other impurities, said other impurities comprising carbon dioxide;
passing said second partially purified stream through said third adsorption medium to selectively remove carbon dioxide from said second partially purified stream, thereby producing said high purity acetylene; and
providing the high purity acetylene to said work device.

17. The method of claim 16 further comprising:
stopping the passing of said stream through said adsorbent bed;
regenerating in-situ said adsorption media, and
removing desorbed impurities from said adsorbent bed.

18. The method of claim 16 wherein said work device is a semiconductor processing tool.

19. The method of claim 16 wherein said high purity acetylene is provided to said work device for use in amorphous carbon hardmask film deposition or for use in depositing carbon and carbon-containing films.

20. A high purity acetylene delivery system comprising:
a storage source containing acetylene and impurities, said impurities comprising moisture and solvent;
a distribution line disposed between said storage source and an adsorbent bed for distributing a stream of acetylene and impurities from said storage source to said adsorbent bed;
said adsorbent bed containing adsorption media capable of removing impurities from said stream;
said adsorption media comprising at least a first adsorption medium for selectively removing moisture from said stream, a second adsorption medium for selectively removing solvent from said stream, and a third adsorption medium for selectively removing other impurities from said stream; and
a second distribution line disposed between said adsorbent bed and a work device for delivering high purity acetylene to said work device.

* * * * *